US009957222B2

(12) United States Patent
Mouloungui et al.

(10) Patent No.: US 9,957,222 B2
(45) Date of Patent: May 1, 2018

(54) ORGANIC OLIGOMERS OF ACYLGLYCEROL

(71) Applicants: AGRONUTRITION, Carbonne (FR); INSTITUT NATIONAL POLYTECHNIQUE DE TOULOUSE, Toulouse (FR); INSTITUT NATIONAL DE LA RECHERCHE AGRONOMIQUE, Paris (FR)

(72) Inventors: Zephirin Mouloungui, Toulouse (FR); Zaher Abdel Baki, Toulouse (FR); Romain Valentin, Toulouse (FR); Bachar Zebib, Toulouse (FR)

(73) Assignees: Agronutrition, Carbonne (FR); Institut National Polytechnique de Toulouse, Toulouse (FR); Institut National de la Recherche Agronomique, Paris (FR)

( * ) Notice: Subject to any disclaimer, the term of this patent is extended or adjusted under 35 U.S.C. 154(b) by 119 days.

(21) Appl. No.: 14/774,570

(22) PCT Filed: Mar. 12, 2014

(86) PCT No.: PCT/FR2014/050564

§ 371 (c)(1),
(2) Date: Sep. 10, 2015

(87) PCT Pub. No.: WO2014/140481

PCT Pub. Date: Sep. 18, 2014

(65) Prior Publication Data

US 2016/0031794 A1 Feb. 4, 2016

(30) Foreign Application Priority Data

Mar. 14, 2013 (FR) ..................................... 13 52296

(51) Int. Cl.

| | |
|---|---|
| ***C07C 69/708*** | (2006.01) |
| ***C07C 59/305*** | (2006.01) |
| ***C08G 64/02*** | (2006.01) |
| ***C08G 64/42*** | (2006.01) |

(52) U.S. Cl.

CPC .......... *C07C 69/708* (2013.01); *C07C 59/305* (2013.01); *C08G 64/0216* (2013.01); *C08G 64/42* (2013.01)

(58) Field of Classification Search

CPC . C07C 69/708; C07C 59/305; C08G 64/0216; C08G 64/42

See application file for complete search history.

(56) References Cited

U.S. PATENT DOCUMENTS

2009/0036642 A1 2/2009 Truong Dinh et al.
2009/0054271 A1 2/2009 Dinh et al.

FOREIGN PATENT DOCUMENTS

FR 2 874 217 A1 2/2006
FR 2 880 025 A1 6/2006

OTHER PUBLICATIONS

Yoshikawa et al. "Synthesis of linear polyglycerols and their esters having single and fine structure" Toyama Kenritsu Daigaku Kiyo (2008), 18, 50-56.*
International Search Report, dated May 8, 2014, from corresponding PCT application.

* cited by examiner

*Primary Examiner* — Joseph R Kosack
(74) *Attorney, Agent, or Firm* — Young & Thompson

(57) ABSTRACT

Organic oligomers of acylglycerol having general formula (I): Formula (I), in which M1 and Q1 are organic groups; G11 is a hydroxylpropyl group; G12 and G13 are α/α'-acylglycerols; n is a natural integer from the range [0; 8]; m is a natural integer from the range [0; 4]; and p is a natural integer from the range [0; 3].

19 Claims, 1 Drawing Sheet

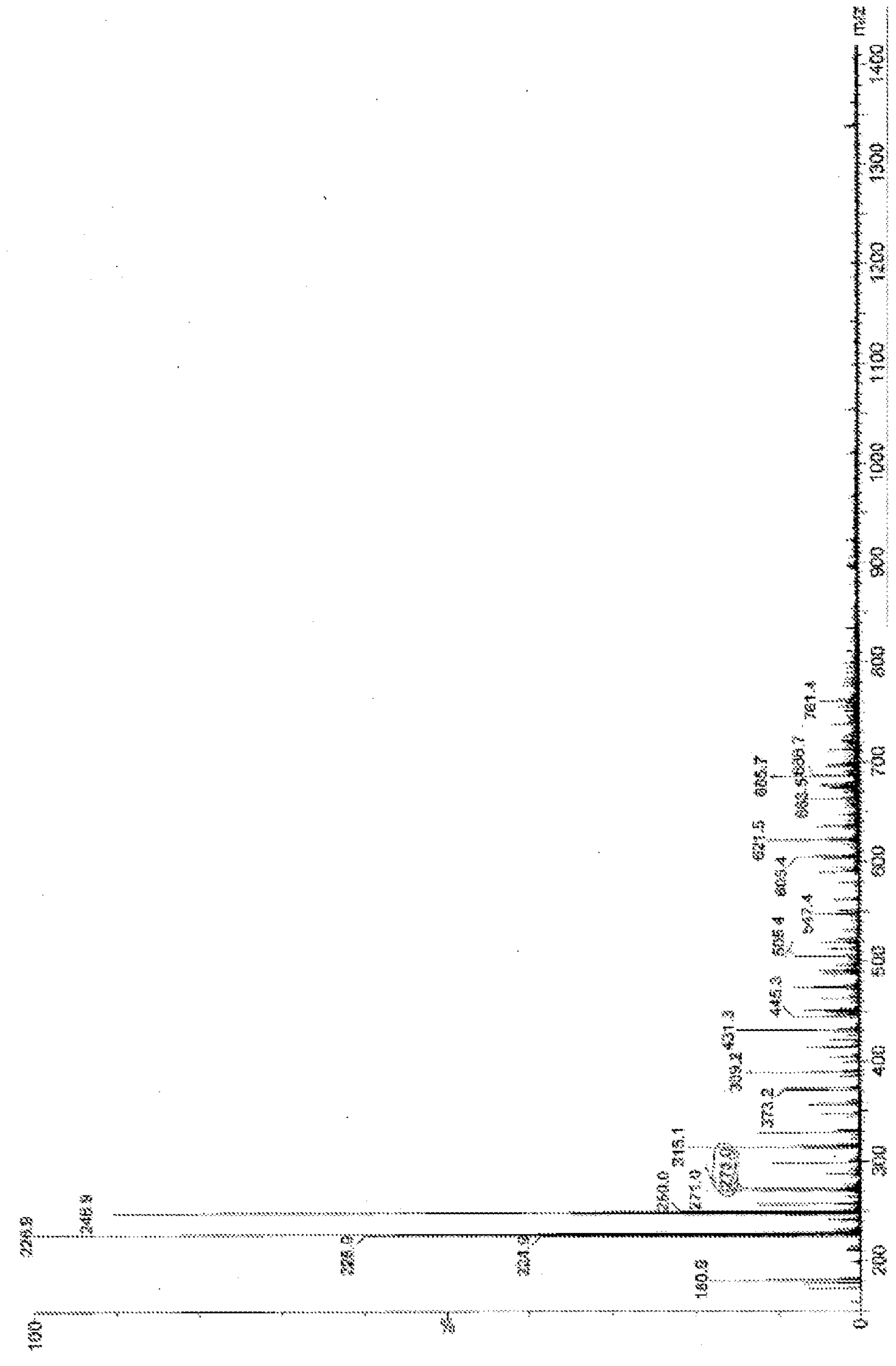
100
%
0
m/z
200
300
400
500
600
700
800
900
1000
1100
1200
1300
1400
228.9
246.9
180.9
260.0
271.0
315.1
373.2
389.2
431.3
445.3
505.4
547.4
603.4
621.5
665.7
761.4

ORGANIC OLIGOMERS OF ACYLGLYCEROL

FIELD OF THE INVENTION

The invention relates to acylated organic glycerol oligomers. In particular, the invention relates to a new family of acylated organic glycerol oligomers which are obtainable by a synthesis process which is simple, economical and respects the environment, especially in a single step. The invention relates also to an organic composition comprising at least one acylated organic glycerol oligomer and more particularly a plurality of acylated organic glycerol oligomers.

BACKGROUND OF THE INVENTION

Partially acylated glycerol carbonate oligomers obtained by partial acylation of glycerol carbonate oligomers are already known (FR 2 880 025). Such partially acylated oligomers obtained in the examples of FR 2 880 025 do not have at least one end of the main oligomer chain that is acylated.

SUMMARY OF THE INVENTION

Accordingly, the invention aims to propose acylated organic glycerol oligomers that have at least one—especially two—end(s) of the main chain that is(are) acylated.

The invention aims also to propose organic oligomers which are not toxic to humans and their environment, which are biodegradable, and which do not accumulate in the environment after they have been used.

In particular, the invention aims also to propose organic oligomers which can be used as adjuvants which do not pose health risks for humans and/or animals.

In particular, the invention aims also to propose organic oligomers which can be prepared in a simple manner starting from resources which are not fossil resources and which are therefore renewable.

In particular, the invention aims also to propose a family of acylated organic glycerol oligomers which are polyfunctional and compatible—especially miscible—with a polar medium and with a non-polar medium. Accordingly, the invention relates to acylated organic glycerol oligomers which are, by nature, amphiphilic.

In particular, the invention aims also to propose such a family of acylated organic glycerol oligomers which can be used as a lubricant. In particular, the invention aims also to propose such a family of acylated organic glycerol oligomers which can be used as a wetting agent for a hydrophobic surface.

In particular, the invention aims also to propose such a family of acylated organic glycerol oligomers which can be used as an input in agriculture, in particular as an adjuvant for the treatment of plants.

In particular, the invention aims also to propose such a family of acylated organic glycerol oligomers which are obtainable by chemical synthesis starting from natural resources—especially plant resources—which are renewable, in particular starting from coproducts of the oleochemical industry.

In particular, the invention aims also to propose a composition comprising at least one oligomer according to the invention—especially an organic composition comprising a plurality of distinct oligomers according to the invention—obtained directly from a synthesis of those oligomers, and which can be used directly—especially which does not require, for its use, a step of purification of each of the acylated organic glycerol oligomers formed in the synthesis.

The invention aims also to propose such a family of acylated organic glycerol oligomers which have a low cost price.

In particular, the invention aims also to propose such a family of acylated organic glycerol oligomers which are obtainable when a process for the synthesis of acylated organic glycerol oligomers in a single step is carried out.

DETAILED DESCRIPTION OF THE INVENTION

To that end, the invention relates to acylated organic glycerol oligomers of the following general formula (I):

(I)

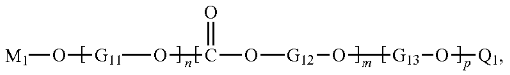

wherein $M_1$ is an organic group chosen from the group formed of the groups of the following formulae:

($I_A$)

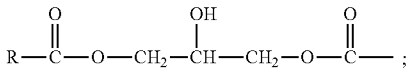

($I_B$)

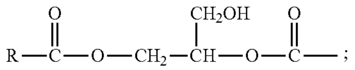

($I_C$)

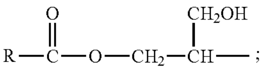

and ($I_D$)

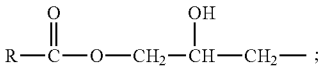

wherein R is a hydrocarbon group—especially a saturated hydrocarbon group, an unsaturated hydrocarbon group, or a branched hydrocarbon group—having from 1 to 21 carbon atoms; and $G_{11}$ is chosen from the group formed of the hydroxylated propyl groups of the following general formulae ($II_A$) and ($II_B$):

($II_A$)

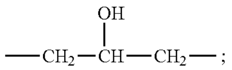

and ($II_B$)

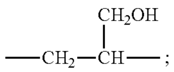

$G_{12}$ and $G_{13}$ are α/α'-hydroxyacylated propyl groups of the following general formula (III):

(III)

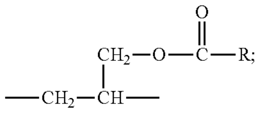

and $Q_1$ is chosen from the group formed of hydrogen and organic groups formed of at least two atoms bonded by covalent bonds and belonging to the group formed of carbon (C), hydrogen (H) and oxygen (O);

n is a natural integer less than 9—that is to say of the interval [0; 8]—such that if n=0 and m≠0, then $M_1$ is chosen from the group formed of $I_C$ and $I_D$, and m is a natural integer less than 5—especially of the interval [0; 4]; and p is a natural integer less than 4—especially of the interval [0; 3].

In the following, the asymmetric groups $G_{11}$ of formula ($II_B$), $G_{12}$ and $G_{13}$ of formula (III) define one or other of the two possible directions of insertion of the group $G_{11}$ of formula ($II_B$) and of groups $G_{12}$ and $G_{13}$ of formula (III) in the acylated organic glycerol oligomer. The asymmetric group $G_{11}$ of formula ($II_B$) defines either of the following two general structures (a) and (b):

(a)

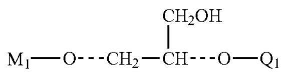

and (b)

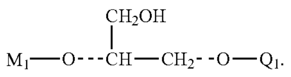

The asymmetric groups $G_{12}$ and $G_{13}$ of formula (III) define either of the following two general structures (c) and (d):

(c)

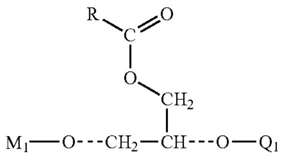

and (d)

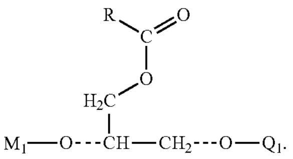

Group $G_{11}$ of formula ($II_A$) can have a single direction of orientation in the acylated organic glycerol oligomer. For example, all the hydroxylated propyl groups of formula ($II_A$) can be oriented in the acylated organic glycerol oligomer in direction (a). All the hydroxylated propyl groups of formula ($II_A$) can be oriented in the acylated organic glycerol oligomer in direction (b). The hydroxylated propyl groups of formula ($II_A$) can also be oriented in the acylated organic glycerol oligomer regularly or irregularly in direction (a) or in direction (b).

Groups $G_{12}$ and $G_{13}$ of formula (III) can have a single direction of orientation in the acylated organic glycerol oligomer. For example, all the groups $G_{12}$ and $G_{13}$ of formula (III) can be oriented in the acylated organic glycerol oligomer in direction (c). In a variant, all the groups $G_{12}$ and $G_{13}$ of formula (III) can be oriented in the acylated organic glycerol oligomer in direction (d). Groups $G_{12}$ and $G_{13}$ of formula (III) can also be oriented in the acylated organic glycerol oligomer regularly or irregularly in direction (c) or in direction (d).

The inventors have observed that it is possible to synthesize such acylated organic glycerol oligomers starting from glycerol, at least one precursor chosen from the group formed of cyclic glycerol carbonic esters and cyclic α/α'-acylated glycerol carbonic esters, and at least one metal catalyst chosen from the group formed of zinc stearate and zinc sulfate. Such acylated organic glycerol oligomers according to the invention are formed by bringing into contact each cyclic glycerol carbonic ester, each cyclic α/α'-acylated glycerol carbonic ester, each metal catalyst, and glycerol in a reactor; said reactor is then closed in order to form in the reactor a vessel that is hermetically sealed to gases, and then the mixture of the precursor(s), the metal catalyst(s) and glycerol is heated in such a manner that the temperature in the reactor reaches a reaction temperature of from 150° C. to 220° C. and in such a manner as to place the liquid mixture under pressure, called autogenous pressure, in said reactor, and then the pressure inside the reactor is adjusted to a value between the value of the autogenous pressure and atmospheric pressure for a period necessary to permit the formation of at least one acylated organic glycerol oligomer of formula (I) according to the invention.

It is possible, therefore, to obtain such acylated organic glycerol oligomers which are polyfunctional, in particular amphiphilic, organic compounds formed of substantially hydrophilic groups and hydrophobic groups by a one-pot process and in a single step and starting from natural resources, in particular plant resources.

Advantageously and according to the invention, $Q_1$ is chosen from the group formed of hydrogen (H), hydroxylated propyl groups of the following formula ($III_A$):

($III_A$)

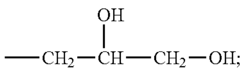

hydroxylated propyl groups of the following formula ($III_B$):

($III_B$)

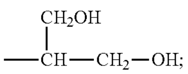

and groups of formulae ($I_A$), ($I_B$), ($I_C$) and ($I_D$).

Advantageously and according to the invention, when m=p=0 and $M_1$ is of formula ($I_A$), then $Q_1$ is hydrogen (H). The acylated organic glycerol oligomer of formula (I) according to the invention is an acylated glycerol carbonic ester of the following general formula (IV):

(IV)

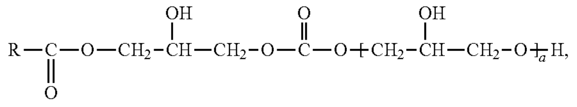

wherein a is a non-zero integer less than 9.

Advantageously and according to the invention, when m=0 and $M_1$ is of formula ($I_B$), then $Q_1$ is hydrogen (H). The acylated organic glycerol oligomer of formula (I) according to the invention is an acylated glycerol carbonic ester of the following general formula (V):

(V)

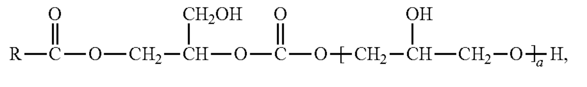

wherein a is a non-zero integer less than 9.

Advantageously and according to the invention, when m=p=0 and $M_1$ is of formula ($I_C$), then $Q_1$ is a group of the general formula ($I_C$). The acylated organic glycerol oligomer of formula (I) according to the invention is of the following general formula (VI):

(VI)

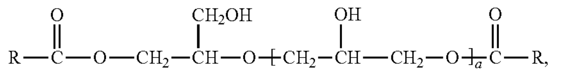

wherein a is a non-zero integer less than 4, especially less than 2.

Such acylated organic glycerol oligomers of formulae (I), (IV), (V), (VI) above or of formulae (VII), (VIII), (IX), (X), (XI), (XII) are formed by bringing into contact each cyclic glycerol carbonic ester, each cyclic α/α'-acylated glycerol carbonic ester, each metal catalyst, and glycerol in a reactor; said reactor is then closed in order to form in the reactor a vessel that is hermetically sealed to gases, and then the mixture of the precursor(s), the metal catalyst(s) and glycerol is heated in such a manner that the temperature in the reactor reaches a reaction temperature of from 150° C. to 220° C. and in such a manner as to place the liquid mixture under pressure, called autogenous pressure, in said reactor, and then the pressure inside the reactor is adjusted to a value between the value of the autogenous pressure and atmospheric pressure for a period necessary to permit the formation of at least one acylated organic glycerol oligomer of formula (I) according to the invention.

The inventors have observed that, advantageously, the adjustment—especially by establishing an efflux of gaseous composition from the reactor—of the pressure inside the reactor to a value between the value of the autogenous pressure and atmospheric pressure allows the formation of linear α/α'-acylated glycerol carbonic esters to be controlled.

In particular, when the mixture formed reaches the reaction temperature and the autogenous pressure, the reactor is opened in order to lower the pressure inside the reactor. To that end:

- an efflux of gaseous composition from the reactor is carried out in order to adjust the pressure of said reactor to a pressure value between the value of atmospheric pressure and the value of the autogenous pressure reached in the closed reactor at the reaction temperature; and
- the reaction temperature is maintained for a period adapted to permit the formation of at least one acylated organic glycerol oligomer according to the invention.

Advantageously, the acylated organic glycerol oligomer of the general formula (I) is a linear α/α'-acylated glycerol carbonic ester.

Advantageously, when a zinc metal catalyst is used (for example ZnO, $Zn(C_{18}H_{35}O_2)_2$ and $ZnSO_4$), there is obtained a mixture of oligomers of formula (I) wherein $M_1$ is of formula ($I_A$), ($I_B$), ($I_C$) or ($I_D$), $Q_1$ is of formula ($I_A$), ($I_B$), ($I_C$), ($I_D$), $G_{11}$ or H, n is a natural integer of the interval [0; 8], m is a natural integer of the interval [0; 4], p is a natural integer of the interval [0; 3].

Advantageously, when a non-zinc metal catalyst is used ($FeSO_4$, $MnSO_4$, $CaCO_3$ and $Na_2CO_3$), there is obtained a mixture of oligomers of formula (I) wherein $M_1$ is of formula ($I_C$) or ($I_D$), $Q_1$ is of formula ($I_C$), ($I_D$), $G_1$ or H, n is a natural integer of the interval [0; 8], m=0, p is a natural integer of the interval [0; 3].

Advantageously and in a variant according to the invention, in the general formula (I), $M_1$ and $Q_1$ are of formula ($I_A$), $G_{11}$ is of formula ($II_A$), $G_{12}$ is of formula (III), n=1, m is a natural integer of the interval [1; 4] and p=0. Such an acylated organic glycerol oligomer is in particular a linear α/α'-acylated glycerol carbonic ester of formula (VII) below:

(VII)

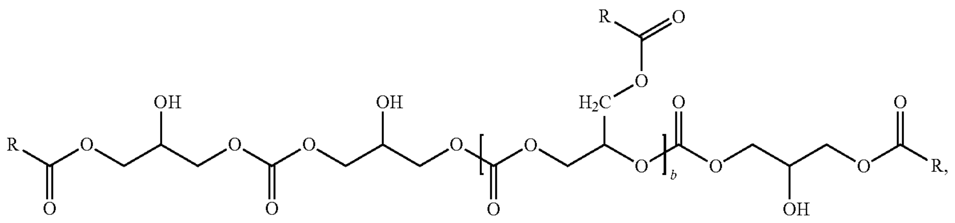

wherein b is a non-zero integer less than 5.

Advantageously and in a variant according to the invention, in the general formula (I), $M_1$ and $Q_1$ are of formula ($I_A$), $G_{11}$ is of formula ($II_B$), $G_{12}$ is of formula (III), n=1, m is a natural integer of the interval [1; 4] and p=0. Such an acylated organic glycerol oligomer is a linear α/α'-acylated glycerol carbonic ester of formula (VIII) below:

(VIII)

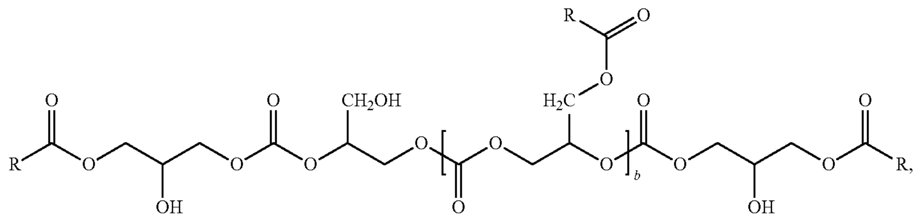

wherein b is a non-zero integer less than 5.

Advantageously and in a variant according to the invention, in the general formula (I), $M_1$ and $Q_1$ are of formula ($I_A$), $G_{11}$ is of formula ($II_A$), $G_{12}$ is of formula (III), n=1, m is a natural integer of the interval [1; 4] and p=0. Such an acylated organic glycerol oligomer is a linear α/α'-acylated glycerol carbonic ester of formula (IX) below:

(IX)

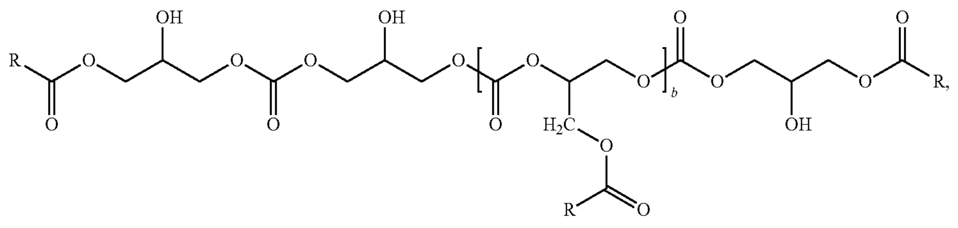

wherein b is a non-zero integer less than 5.

Advantageously and in a variant according to the invention, in the general formula (I), $M_1$ and $Q_1$ are of formula ($I_A$), $G_{11}$ is of formula ($II_B$), $G_{12}$ is of formula (III), n=1, m is a natural integer of the interval [1; 4] and p=0. Such an acylated organic glycerol oligomer is a linear α/α'-acylated glycerol carbonic ester of formula (X) below:

(X)

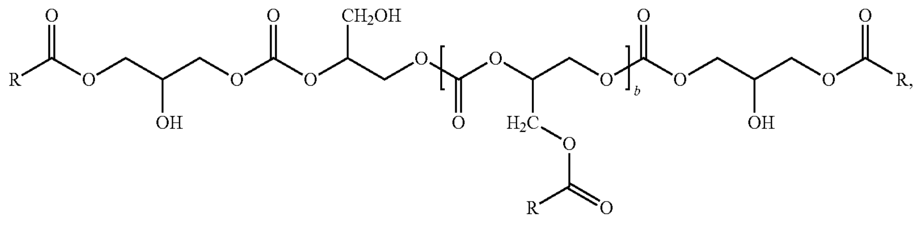

wherein b is a non-zero integer less than 5.

Advantageously and in a variant according to the invention, in the general formula (I), $M_1$ is of formula ($I_B$), $Q_1$ is of formula ($I_A$), $G_{11}$ is of formula ($II_A$), $G_{12}$ is of formula (III), n=1, m is a natural integer of the interval [1; 4] and p=0. Such an acylated organic glycerol oligomer is a linear α/α'-acylated glycerol carbonic ester of formula (XI) below:

(XI)

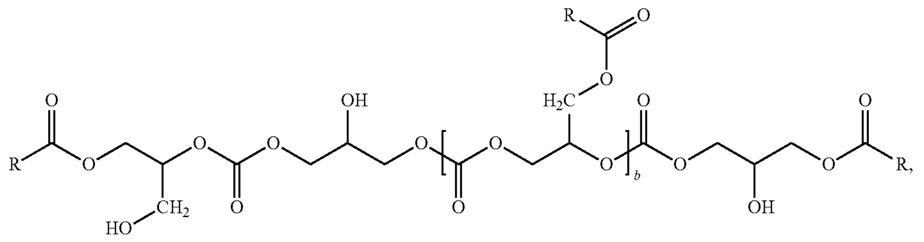

wherein b is a non-zero integer less than 5.

Advantageously and in a variant according to the invention, in the general formula (I), $M_1$ is of formula ($I_B$), $Q_1$ is of formula ($I_A$), $G_{11}$ is of formula ($II_B$), $G_{12}$ is of formula (III), n=1, m is a natural integer of the interval [1; 4] and p=0. Such an acylated organic glycerol oligomer is a linear α/α'-acylated glycerol carbonic ester of formula (XII) below:

(XII)

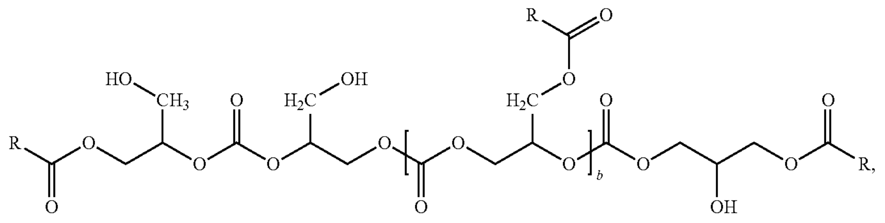

wherein b is a non-zero integer less than 5.

Advantageously and in a variant according to the invention, in the general formula (I), $M_1$ is of formula ($I_B$), $Q_1$ is of formula ($I_A$), $G_{11}$ is of formula ($II_A$), $G_{12}$ is of formula (III), n=1, m is a natural integer of the interval [1; 4] and p=0. Such an acylated organic glycerol oligomer is a linear α/α'-acylated glycerol carbonic ester of formula (XIII) below:

(XIII)

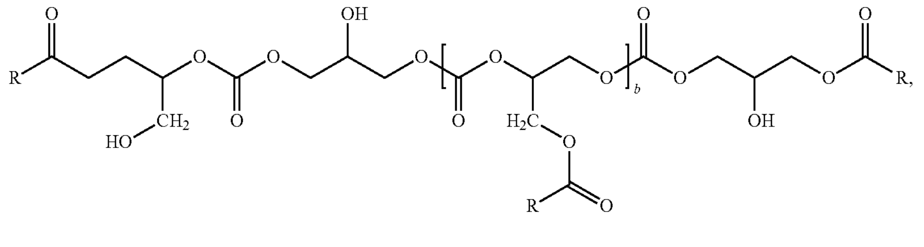

wherein b is a non-zero integer less than 5.

Advantageously and in a variant according to the invention, in the general formula (I), $M_1$ is of formula ($I_B$), $Q_1$ is of formula ($I_A$), $G_{11}$ is of formula ($II_B$), $G_{12}$ is of formula (III), n=1, m is a natural integer of the interval [1; 4] and p=0. Such an acylated organic glycerol oligomer is a linear α/α'-acylated glycerol carbonic ester of formula (XIV) below:

(XIV)

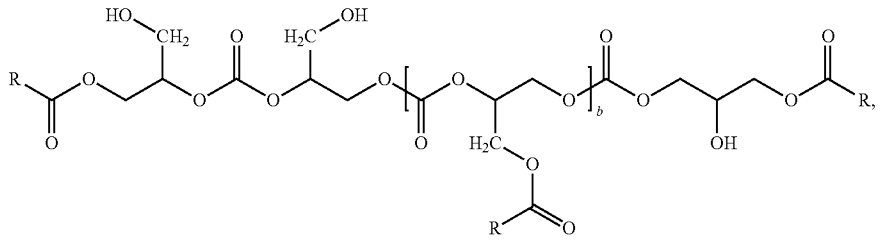

wherein b is a non-zero integer less than 5.

Advantageously and according to the invention, R is a hydrocarbon group chosen from the group formed of:

saturated hydrocarbon groups of the general formula $—C_qH_{2q}+1$ wherein q is an integer from 1 to 21; and unsaturated hydrocarbon groups—especially monounsaturated hydrocarbon groups of the general formula $—C_sH_{2s-1}$ wherein s is an integer from 1 to 21, and polyunsaturated hydrocarbon groups.

Advantageously and according to the invention, R is a hydrocarbon group chosen from the group formed of methyl ($—CH_3$), ethyl ($—CH_2—CH_3$), n-propyl ($—CH_2—CH_2—CH_3$), iso-propyl ($—CH(CH_3)_2$), n-butyl ($—CH_2—CH_2—CH_2—CH_3$), iso-butyl ($—CH_2—CH(CH_3)_2$), tert-butyl ($—C(CH_3)_3$), n-pentyl ($—CH_2—(CH_2)_3—CH_3$), hexyl ($—(CH_2)_5—CH_3$), octyl ($—(CH_2)_7—CH_3$), undecyl ($—(CH_2)_{10}—CH_3$), pentadecyl ($—(CH_2)_{14}—CH_3$), heptadecyl ($—(CH_2)_{16}—CH_3$) and their unsaturated equivalents—especially 9-ene-decyl ($—CH{=}CH—(CH_2)_7—CH_3$) and 9-ene-heptadecyl ($—(CH_2)_7—CH{=}CH—(CH_2)_7—CH_3$).

Advantageously and according to the invention, the acylated organic glycerol oligomer of the general formula (I) has a molar mass greater than 400 g/mol.

The invention relates also to a liquid organic composition comprising at least one acylated organic glycerol oligomer according to the invention. In particular, it relates to a liquid organic composition comprising a plurality of acylated organic glycerol oligomers according to the invention.

The invention relates also to an acylated organic glycerol oligomer and to a liquid organic composition comprising at least one such acylated organic glycerol oligomer, characterized in combination by all or some of the features mentioned hereinabove or hereinbelow.

Other objects, features and advantages of the invention will become apparent upon reading the following description and the following examples, which are given without implying any limitation and in which FIG. 1 is a mass spectrogram of a reaction mixture formed by carrying out a process according to the invention.

EXAMPLE 1

Synthesis of (Cyclic) α/α'-Acylated Glycerol Carbonic Esters as Precursor

The synthesis of (cyclic) α/α'-acylated glycerol carbonic esters, in particular of α/α'-heptanoic glycerol carbonic ester (ECG-C7), a/a'-nonanoic glycerol carbonic ester (ECG-C9), α/α'-undecylenoic glycerol carbonic ester (ECG-C11:1) and α/α'-oleic glycerol carbonic ester (ECG-C18:1), is carried out by esterification of the cyclic α/α'-hydroxylated glycerol carbonate with the corresponding fatty acid.

1.64 mol of fatty acid and 0.0078 mol of 4-methylbenzenesulfonic acid (CAS no. 6192-52-5, para-toluenesulfonic acid, ApTs) are placed in a 500 ml reactor equipped with a mechanical stirring device, a device for placing under reduced pressure and a "Dean-Stark" device for removing the water that forms. The temperature of the mixture is brought to a temperature of 110° C. under reduced pressure of 800 hPa for a period of 15 minutes. 0.84 mol of (cyclic) α/α'-hydroxylated glycerol carbonate is then added dropwise to the reactor with mechanical stirring at 800 revolutions per minute (rpm) over a period of 15 minutes. The reactor is placed in an oil bath brought to a temperature of 110° C. with mechanical stirring (800 rpm) for 3 hours.

EXAMPLE 2

Purification of the (Cyclic) α/α'-Acylated Glycerol Carbonic Esters

The reaction mixture is diluted in 150 ml of ethyl ether, and the mixture obtained is placed in a 1 liter separating funnel. The mixture is washed in succession with 4 volumes of water saturated with NaCl until the aqueous phase is neutral. The washed organic phase is dried over magnesium sulfate and then separated from the hydrated magnesium sulfate by filtration. The ether of the organic phase is removed by evaporation under reduced pressure. A mass of dry product of 277 g is obtained. The (cyclic) α/α'-acylated glycerol carbonic ester is separated from the excess fatty acids by thin film distillation under reduced pressure (0.6 hPa) at a temperature that is below the boiling point of the fatty acid under that reduced pressure and below 155° C. The (cyclic) α/α'-acylated glycerol carbonic ester is obtained, the purity of which, evaluated by gas phase chromatography, is from 85% to 95%.

EXAMPLE 3

Synthesis of the Cyclic α/α'-Acetylated Glycerol Carbonic Ester (ECG-C2)

472 g of cyclic glycerol carbonate (4-(hydroxymethyl)-1,3-dioxolan-2-one, CAS 931-40-8) and 4 g of Lewatit K2431 resin are placed in a 2-liter three-necked glass flask equipped with a mechanical stirrer and with a coolant and placed in an oil bath. 6 mol of acetic anhydride are added dropwise to the reactor in such a manner as to control and maintain the temperature of the reactor at 50° C., with mechanical stirring at 800 rpm for 4 hours.

The excess acetic anhydride is removed by evaporation at a temperature of 60° C. and under reduced pressure of 55 hPa. The linear α/α'-acetylated glycerol carbonic ester is purified by the thin film technique carried out in an evaporator/separator at a temperature of 170° C. and under reduced pressure of 0.33 hPa. The α/α'-acetylated glycerol carbonic ester is obtained, the purity of which, evaluated by gas phase chromatography, is from 98% to 99%.

The structural characteristics of the (cyclic) α/α'-acylated glycerol carbonic esters obtained in Examples 1, 2 and 3 are given in Table 1 below.

TABLE 1

| | Purity, % | $^{13}C$, $^{1}H$ NMR | FTIR | Mass spectrometry, m/z |
|---|---|---|---|---|
| ECG-C2 | 98 | conforms | conforms | 160.1 |
| ECG-C7 | 94 | conforms | conforms | 230.2 |
| ECG-C9 | 95 | conforms | conforms | 258.3 |
| ECG-C11:1 | 85 | conforms | conforms | 284.3 |
| ECG-C18:1 | 96 | conforms | conforms | 382.5 |

EXAMPLE 4

Oligomerization of the (Cyclic) α/α-Acetylated Glycerol Carbonic Ester (ECG-C2)

The oligomerization of the α/α-acetylated glycerol carbonic ester (ECG-C2) obtained in Example 3 is carried out in the presence of a metal catalyst and of glycerol as organic initiator, under the conditions described in Table 2 below.

TABLE 2

| | Metal catalyst | | | | | Number-average |
|---|---|---|---|---|---|---|
| Mass ECG-C2, g | Type | Mass, mg | Initiator Glycerol, g | Conditions | TC, % | molar masses |
| 4.25 | Zinc stearate $Zn(C_{18}H_{35}O_2)_2$ | 25 | 1.5 | 160° C., $P_{atm}$, 2 h | 59 | 393, 195, 64 |
| 8.5 | $Zn(C_{18}H_{35}O_2)_2$ | 25 | 1.5 | 160° C., $P_{atm}$, 2 h | 95 | 970, 688, 352, 274, 202, 190 |
| 42.5 | $Zn(C_{18}H_{35}O_2)_2$ | 250 | 7.5 | 160° C., 1800 hPa, 2 h | 61 | 321, 157, 91 |
| 21.25 | $Zn(C_{18}H_{35}O_2)_2$ | 125 | 3.75 | 160° C., $P_{atm}$, 2 h | 84 | 714, 336, 206, 139, 92 |
| 21.5 | $Zn(C_{18}H_{35}O_2)_2$ | 125 | 3.75 | 160° C., $P_{atm}$, 2 h | 99.2 | 405, 253, 172, 93 |
| 21.5 | $Zn(C_{18}H_{35}O_2)_2$ | 125 | 3.75 | 160° C., $P_{atm}$, 2 h | 98.4 | 574, 320, 160, 95 |
| 21.5 | $Zn(C_{18}H_{35}O_2)_2$ | 125 | 3.75 | 160° C., $P_{atm}$, 2 h | 98.4 | 395, 189, 140, 92 |
| 8.5 | $ZnSO_4$ | 50 | 1.75 | 160° C., 3400 hPa, 2 h | 76 | 420, 173, 122, 84, 36 |
| 9 | $ZnSO_4$ | 50 | 1.7 | 160° C., $P_{atm}$, 30 h | 55 | 431, 160, 83 |
| 21.25 | $ZnSO_4$ | 125 | 3.75 | 160° C., $P_{atm}$, 2 h | 66 | 389, 159, 83 |
| 21.5 | $FeSO_4$ $8H_2O$ | 60 | 3.75 | 160° C., $P_{atm}$, 2 h | 40.3 | 446, 162, 96 |
| 21.5 | ZnO | 55 | 3.75 | 160° C., $P_{atm}$, 2 h | 46 | 322, 156, 95 |
| 21.5 | $MnSO_4$, $1H_2O$ | 118 | 3.75 | 160° C., $P_{atm}$, 2 h | 51 | 327, 156, 96 |
| 21.5 | $MnSO_4$, $1H_2O$ | 85 | 3.75 | 160° C., $P_{atm}$, 2 h | 34 | 323, 154, 94 |
| 21.5 | $ZnSO_4$, $1H_2O$ | 125 | 3.75 | 160° C., $P_{atm}$, 2 h | 36 | 327, 157, 94 |
| 21.5 | $CaCO_3$ | 70 | 3.75 | 160° C., $P_{atm}$, 2 h | 31 | 324, 154, 94 |
| 21.5 | $Na_2CO_3$ | 74 | 3.75 | 160° C., $P_{atm}$, 2 h | 98 | 632, 314, 192, 137, 99 |

The value TC (%) indicates the rate of conversion of the starting (cyclic) α/α'-acylated glycerol carbonic ester. The number-average molar mass values are obtained by analysis of the reaction mixture by gel permeation chromatography on a PLgel 3 μm MIXED-E column. The acylated organic glycerol oligomers are detected at the column outlet by refractometry and the number-average molecular masses are determined by comparison with polystyrene standards.

The syntheses carried out with a zinc metal catalyst (ZnO, $Zn(C_{18}H_{35}O_2)_2$ and $ZnSO_4$) yield a mixture of oligomers of formula (I) wherein $M_1$ is of formula ($I_A$), ($I_B$), ($I_C$) or ($I_D$), $Q_1$ is of formula ($I_A$), ($I_B$), ($I_C$), ($I_D$), $G_{11}$ or H, n is a natural integer of the interval [0; 8], m is a natural integer of the interval [0; 4], p is a natural integer of the interval [0; 3] and R is a methyl radical.

An example of a mass spectrum of a reaction mixture obtained by carrying out a process of oligomerization of the α/α'-acetylated glycerol carbonic ester (ECG-C2) as described in Example 4 is shown in FIG. 1. There are detected signals corresponding to molecular ions and fragments of m/z values of from 180.9 to 761.4 and corresponding to organic glycerol oligomers of the following particular formulae (A), (B), (C) and (D):

(A)

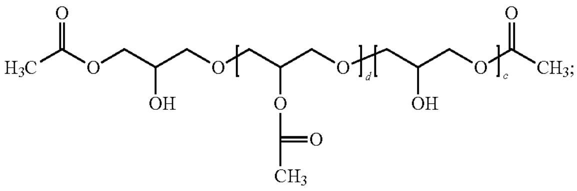

wherein c can have the value 1, 2 or 4 and d can have the value 1, 2, 3 or 4;

(B)

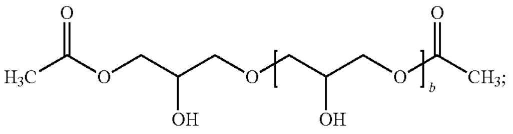

wherein b can have the value 1, 2 or 3;

(C)

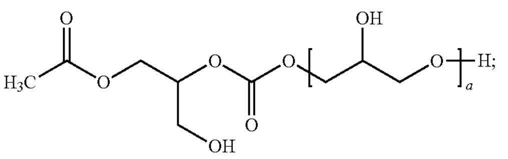

wherein a can have the value 1, 2, 3, 4, 5, 6, 7 or 8; and (D)

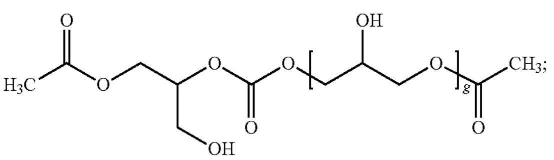

wherein g can have the value 1, 2, 3, 4, 5, 6, 7, 8, 9 or 10.

The syntheses carried out with a non-zinc metal catalyst ($FeSO_4$, $MnSO_4$, $CaCO_3$ and $Na_2CO_3$) yield a mixture of oligomers of formula (I) wherein $M_1$ is of formula ($I_C$) or ($I_D$), $Q_1$ is of formula ($I_C$), ($I_D$), $G_{11}$ or H, n is a natural integer of the interval [0; 8], m=0, p is a natural integer of the interval [0; 3] and R is a methyl radical.

EXAMPLE 5

Oligomerization of (Cyclic) α/α-Acylated Glycerol Carbonic Esters (ECG-C2, ECG-C7, ECG-C9, ECG-C11:1 and ECG-C18:1)

An oligomerization of the (cyclic) α/α'-acylated glycerol carbonic esters is carried out under the conditions described in Table 3 below.

TABLE 3

| ECG, mass | Metal catalyst Type | Mass, mg | Initiator Glycerol, g | Conditions | TC, % | Number-average molar masses |
|---|---|---|---|---|---|---|
| ECG-C2, 21.25 g | $Zn(C_{18}H_{35}O_2)_2$ | 125 | 3.75 | 160° C., $P_{atm}$, 2 h | 98 | 714, 335 206, 139, 92 |
| ECG-C2, 21.25 g | $ZnSO_4$ | 125 | 3.75 | 160° C., $P_{atm}$, 2 h | 66 | 389, 159, 83 |
| ECG-C7, 20 g | $ZnSO_4$ | 113 | 2.42 | 200° C., $P_{atm}$, 2 h | 64 | 639, 420, 252, 96 |
| ECG-C9, 20 g | $ZnSO_4$ | 110 | 2.15 | 180° C., $P_{atm}$, 2 h | 88 | 992, 541, 303, 90 |
| ECG-C11:1, 10 g | $ZnSO_4$ | 86 | 1.3 | 190° C., $P_{atm}$, 2 h | 98 | 7632, 2113, 1084, 750, 486 |
| ECG-C18:1, 10 g | $ZnSO_4$ | 50 | 0.7 | 200° C., $P_{atm}$, 2 h | 97 | 3724, 1787, 1169, 613, 94 |

Oligomers having an apparent molar mass which can reach 7600 Da are obtained.

The syntheses carried out with a zinc metal catalyst ($Zn(C_{18}H_{35}O_2)_2$ and $ZnSO_4$) yield a mixture of oligomers of formula (I) wherein $M_1$ is of formula ($I_A$), ($I_B$), ($I_C$) or ($I_D$), $Q_1$ is of formula ($I_A$), ($I_B$), ($I_C$), ($I_D$), $G_{11}$ or H, n is a natural integer of the interval [0; 8], m is a natural integer of the interval [0; 4], p is a natural integer of the interval [0; 3] and R is chosen from methyl ($—CH_3$), hexyl ($—(CH2)_5—CH_3$), octyl ($—(CH2)_7—CH_3$), 9-ene-decyl ($—CH{=}CH—(CH2)_7—CH_3$) and 9-ene-heptadecyl ($—(CH2)_7—CH{=}CH—(CH2)_7—CH_3$).

The value TC (%) indicates the rate of conversion of the starting (cyclic) α/α'-acylated glycerol carbonic ester. The apparent molar mass values are obtained by analysis of the reaction mixture by gel permeation chromtatography.

It goes without saying that the invention can be the subject of numerous variant embodiments and applications. In particular, the process of synthesis of the linear α/α'-acylated carbonic esters is subject to an infinite number of variants, in particular as regards the reaction temperature, the reaction pressure, the proportion by mass of metal catalyst, of (cyclic) α/α'-acylated glycerol carbonic ester(s) and of organic initiator.

Of course, this description is given only by way of an illustrative example, and the person skilled in the art will be able to provide numerous modifications, variations and applications thereof without departing from the scope of the invention.

The invention claimed is:

1. An acylated organic glycerol oligomer of general formula (I):

(I)

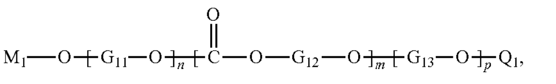

wherein:

$M_1$ is an organic group selected from formulae ($I_A$), ($I_B$), ($I_C$), and ($I_D$):

($I_A$)

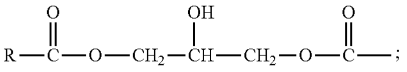

($I_B$)

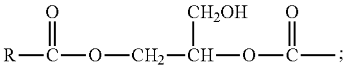

($I_C$)

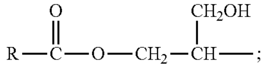

and

-continued ($I_D$)

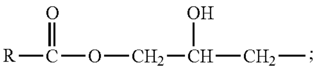

wherein

R is a hydrocarbon group, a saturated hydrocarbon group, an unsaturated hydrocarbon group or a branched hydrocarbon group, having from 1 to 21 carbon atoms;

$G_{11}$ is selected from the of hydroxylated propyl groups of formulae ($II_A$) and ($II_B$):

($II_A$)

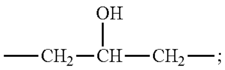

and ($II_B$)

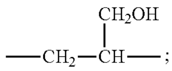

$G_{12}$ and $G_{13}$ are α/α'-hydroxyacylated propyl groups of formula (III):

(III)

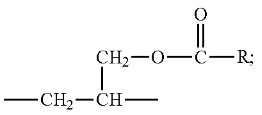

and $Q_1$ is chosen from the group formed of hydrogen and organic groups formed of at least two atoms bonded by covalent bonds and belonging to the group formed of carbon (C), hydrogen (H) and oxygen (O);

n is a natural integer less than 9 such that if n=0, then $M_1$ is of formula ($I_C$) or ($I_D$); and m is a non-zero integer less than 5; and p is an integer less than 4.

2. The oligomer as claimed in claim 1, wherein $Q_1$ is selected from the group consisting of:

hydrogen (H), hydroxylated propyl groups of formula ($III_A$):

($III_A$)

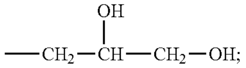

hydroxylated propyl groups of formula ($III_B$):

($III_B$)

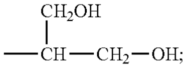

and groups of formulae ($I_A$), ($I_B$), ($I_C$) and ($I_D$).

3. An acylated organic glycerol oligomer of formula (IV):

(IV)

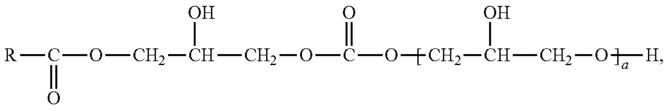

wherein

R is a hydrocarbon group, a saturated hydrocarbon group, an unsaturated hydrocarbon group or a branched hydrocarbon group, having from 1 to 21 carbon atoms; and a is a non-zero integer less than 9.

4. An acylated organic glycerol oligomer of formula (V):

(V)

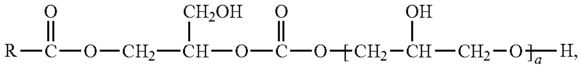

wherein

R is a hydrocarbon group, a saturated hydrocarbon group, an unsaturated hydrocarbon group or a branched hydrocarbon group, having from 1 to 21 carbon atoms; and a is a non-zero integer less than 9.

5. An acylated organic glycerol oligomer of formula (VI):

(VI)

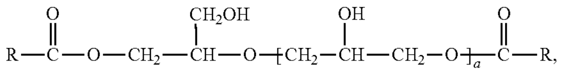

wherein

R is a hydrocarbon group, a saturated hydrocarbon group, an unsaturated hydrocarbon group or a branched hydrocarbon group, having from 1 to 21 carbon atoms; and a is a non-zero integer less than 4.

6. The oligomer claim 1, having the formula (VII):
(VII)
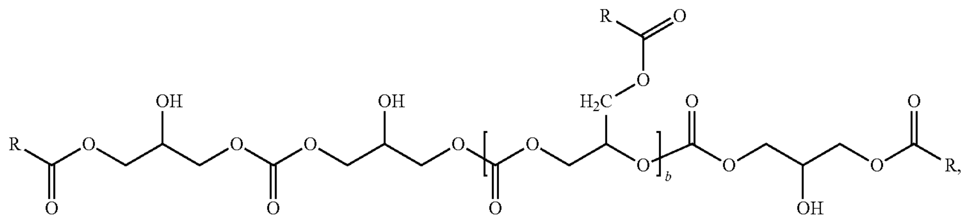
wherein b is a non-zero integer less than 5.
7. The oligomer of claim 1, having the formula (VIII):
(VIII)
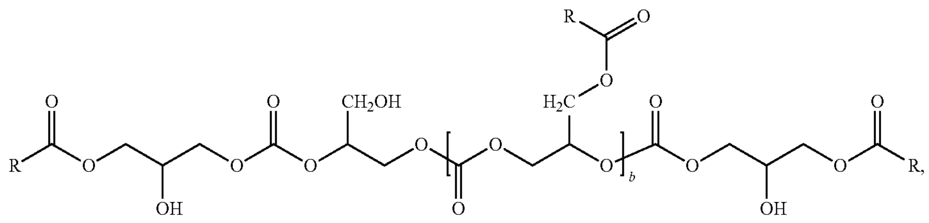
wherein b is a non-zero integer less than 5.
8. The oligomer of claim 1, having the formula (IX):
(IX)
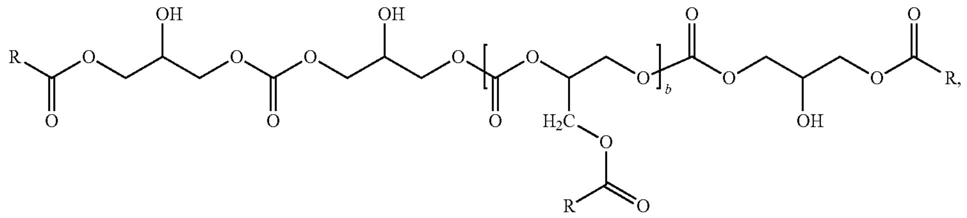
wherein b is a non-zero integer less than 5.
9. The oligomer of claim 1, having the formula (X):
(X)
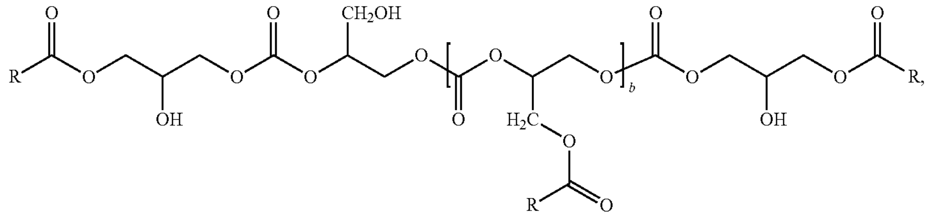
wherein b is a non-zero integer less than 5.

10. The oligomer of claim 1, having the formula (XI):

(XI)

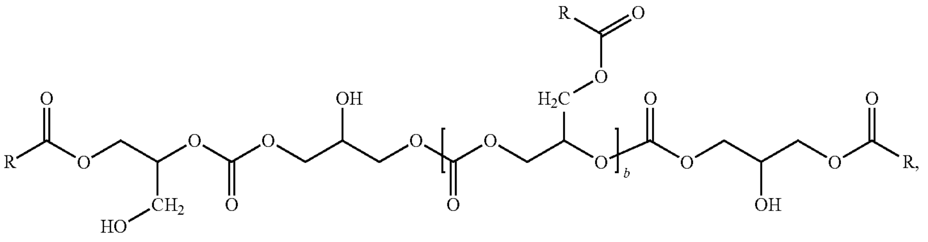

wherein b is a non-zero integer less than 5.

11. The oligomer of claim 1, having the formula (XII):

(XII)

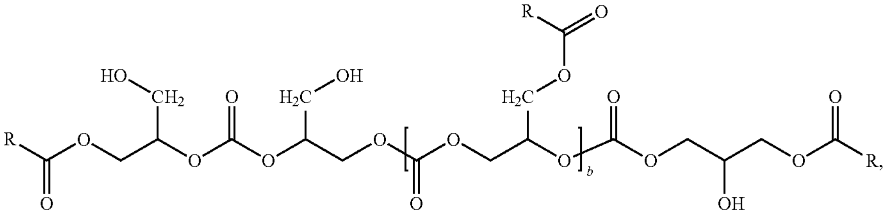

wherein b is a non-zero integer less than 5.

12. The oligomer of claim 1, having the formula (XIII):

(XIII)

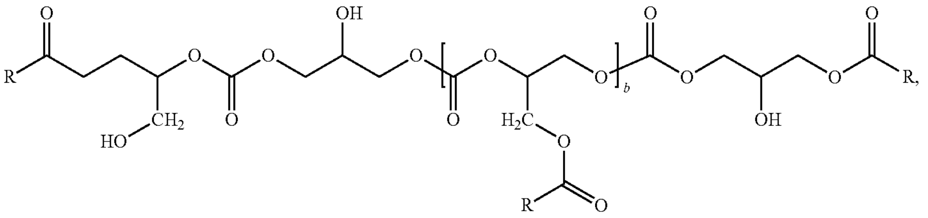

wherein b is a non-zero integer less than 5.

13. The oligomer of claim 1, having the formula (XIV):

(XIV)

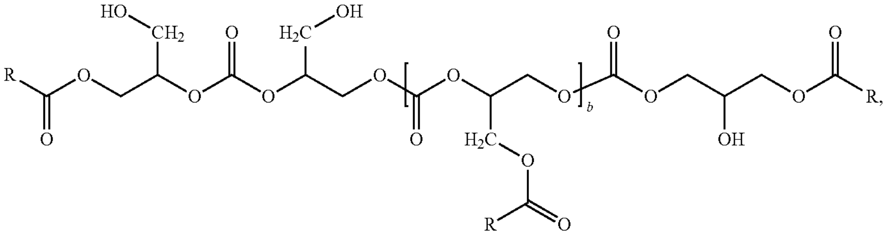

wherein b is a non-zero integer less than 5.

14. The oligomer of claim 1, wherein R is a hydrocarbon group selected from the group consisting of:

saturated hydrocarbon groups of the general formula $—C_qH_{2q+1}$ wherein q is an integer from 1 to 21; and unsaturated hydrocarbon groups, monounsaturated hydrocarbon groups of the general formula $—C_sH_{2s-1}$ wherein s is an integer from 1 to 21, and polyunsaturated hydrocarbon groups.

15. The oligomer of claim 1, wherein R is a hydrocarbon group selected from the group consisting of methyl ($—CH_3$), ethyl ($—CH_2—CH_3$), n-propyl ($—CH_2—CH_2—CH_3$), iso-propyl ($—CH(CH_3)_2$), n-butyl ($—CH_2—CH_2—CH_2—CH_3$), iso-butyl ($—CH_2—CH(CH_3)_2$), tert-butyl ($—C(CH_3)_3$), n-pentyl ($—CH_2—(CH_2)_3—CH_3$), hexyl ($—(CH_2)_5—CH_3$) octyl ($—(CH_2)_7—CH_3$) undecyl ($—(CH_2)_{10}—CH_3$), pentadecyl ($—(CH_2)_{14}—CH_3$) heptadecyl ($—(CH_2)_{16}—CH_3$), 9-ene-decyl ($—CH{=}CH—(CH_2)_7—CH_3$) and 9-ene-heptadecyl ($—(CH_2)_7—CH{=}CH—(CH_2)_7—CH_3$).

16. A liquid organic composition comprising at least one acylated organic glycerol oligomer of claim 1.

17. The composition of claim 16, comprising a plurality of said acylated organic glycerol oligomers.

18. The oligomer of claim 2, wherein R is a hydrocarbon group selected from the group consisting of methyl ($—CH_3$), ethyl ($—CH_2—CH_3$), n-propyl ($—CH_2—CH_2—CH_3$), iso-propyl ($—CH(CH_3)_2$), n-butyl ($—CH_2—CH_2—CH_2—CH_3$), iso-butyl ($—CH_2—CH(CH_3)_2$), tert-butyl ($—C(CH_3)_3$), n-pentyl ($—CH_2—(CH_2)_3—CH_3$), hexyl ($—(CH_2)_5—CH_3$), octyl ($—(CH_2)_7—CH_3$), undecyl ($—(CH_2)_{10}—CH_3$), pentadecyl ($—(CH_2)_{14}—CH_3$), heptadecyl ($—(CH_2)_{16}—CH_3$), 9-ene-decyl ($—CH{=}CH—(CH_2)_7—CH_3$) and 9-ene-heptadecyl ($—(CH_2)_7—CH{=}CH—(CH_2)_7—CH_3$).

19. The oligomer of claim 2, having the following general formula (VII):
(VII)
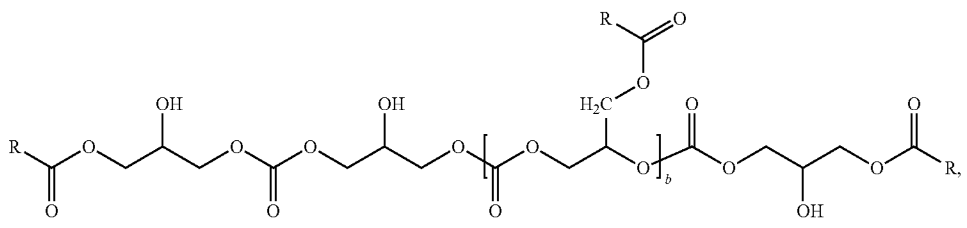
wherein b is a non-zero integer less than 5.
* * * * *

UNITED STATES PATENT AND TRADEMARK OFFICE

CERTIFICATE OF CORRECTION

PATENT NO. : 9,957,222 B2
APPLICATION NO. : 14/774570
DATED : May 1, 2018
INVENTOR(S) : Zephirin Mouloungui et al.

It is certified that error appears in the above-identified patent and that said Letters Patent is hereby corrected as shown below:

In the Claims

In Claim 1, Column 17, Line 36 "-continued" should be deleted.

Signed and Sealed this
Second Day of October, 2018

Andrei Iancu
*Director of the United States Patent and Trademark Office*